(12) United States Patent
Costantino et al.

(10) Patent No.: US 6,284,283 B1
(45) Date of Patent: Sep. 4, 2001

(54) METHOD OF PRODUCING SUB-MICRON PARTICLES OF BIOLOGICALLY ACTIVE AGENTS AND USES THEREOF

(75) Inventors: Henry R. Costantino, Grantham, NH (US); Warren E. Jaworowicz, Boxboro, MA (US); Mark A. Tracy, Arlington, MA (US); Christopher P. Beganski, Littleton, MA (US)

(73) Assignee: Alkermes Controlled Therapeutics, Inc., Cambridge, MA (US)

( * ) Notice: Subject to any disclaimer, the term of this patent is extended or adjusted under 35 U.S.C. 154(b) by 0 days.

(21) Appl. No.: 09/422,751

(22) Filed: Oct. 21, 1999

(51) Int. Cl.$^7$ .............................. A61K 9/50; B32B 5/16; B32B 15/02; B01J 13/02; B01J 13/04

(52) U.S. Cl. .................... 424/501; 424/502; 428/402.21; 264/4.1; 264/4.33; 264/4.6

(58) Field of Search .................... 424/501, 502; 264/4.1, 4.33, 4.6; 428/402.21

(56) References Cited

U.S. PATENT DOCUMENTS

| | | | |
|---|---|---|---|
| 3,313,032 | 4/1967 | Malecki | 34/5 |
| 3,620,776 | 11/1971 | Mishkin et al. | 99/199 |
| 3,928,566 | 12/1975 | Briggs et al. | 424/94 |
| 4,073,158 | 2/1978 | Guiller | 62/266 |
| 4,323,478 | 4/1982 | Adams et al. | 252/408 |
| 4,329,787 | 5/1982 | Newton | 34/1 |
| 4,479,363 | 10/1984 | Gibson et al. | 62/63 |
| 4,704,873 | 11/1987 | Imaike et al. | 62/64 |
| 4,748,817 | 6/1988 | Oura et al. | 62/74 |
| 4,843,840 | 7/1989 | Gibson | 62/375 |
| 4,848,094 | 7/1989 | Davis et al. | 62/64 |
| 5,307,640 | 5/1994 | Fawzy et al. | 62/52.1 |
| 5,475,984 | 12/1995 | Fermani et al. | 62/64 |
| 5,654,010 | 8/1997 | Johnson et al. | 424/502 |
| 5,656,297 | 8/1997 | Bernstein et al. | 424/484 |
| 5,674,534 | 10/1997 | Zale et al. | 424/501 |
| 5,711,968 | 1/1998 | Tracy et al. | 424/487 |
| 5,727,333 | 3/1998 | Folan | 34/285 |
| 5,817,343 | 10/1998 | Burke | 424/489 |
| 5,911,851 | 6/1999 | Bartels et al. | 156/345 |
| 5,912,015 | 6/1999 | Bernstein et al. | 424/484 |
| 5,922,253 | * 7/1999 | Herbert et al. | 264/5 |

FOREIGN PATENT DOCUMENTS

| | | |
|---|---|---|
| 0 478 118 A1 | 7/1991 | (EP). |
| WO 90/13285 | 11/1990 | (WO). |
| WO 93/17668 | 9/1993 | (WO). |
| WO 93/25221 | 12/1993 | (WO). |
| WO 95/29664 | 11/1995 | (WO). |
| WO 96/40074 | 12/1996 | (WO). |

* cited by examiner

*Primary Examiner*—Carlos Azpuru
(74) *Attorney, Agent, or Firm*—Hamilton, Brook, Smith & Reynolds, P.C.

(57) ABSTRACT

Submicron particles of a biologically active agent are prepared by atomizing using multifluid atomization a dispersed system comprising at least one biologically active agent and at least one solvent to produce droplets, freezing the droplets to produce frozen droplets, lyophilizing the frozen droplets to obtain microstructures capable of being further fragmented into submicron particles by techniques such as probe sonication. The submicron particles can be incorporated into sustained release compositions having a reduced initial release of biologically active agent. The sustained release compositions can be administered to a human or animal.

36 Claims, 6 Drawing Sheets

- Treatment Group A (16.5% protein load) p.s. = 0.32 microns
○ Treatment Group B (16.1% protein load) p.s = 1.8 microns
- Treatment Group C (12.5% protein load) p.s. = 2.0 microns
□ Treatment Group D (12.3% protein load) p.s. = 0.45 microns

- Treatment Group E (16.6% protein load) p.s. = 0.23 microns
- ○ Treatment Group F (13% protein load) p.s. = 0.23 microns
- ■ Treatment Group G (16.6% protein load) p.s. = 3.2 microns
- □ Treatment Group H (16.2% protein load) p.s. = 1.8 microns

METHOD OF PRODUCING SUB-MICRON PARTICLES OF BIOLOGICALLY ACTIVE AGENTS AND USES THEREOF

BACKGROUND OF THE INVENTION

It is known in the pharmaceutical industry that the rate of dissolution of a particulate drug can increase with specific surface area (e.g., decreasing particle size). This increase can result in enhanced bioavailability of the particulate drug. In sustained release compositions in which a drug is dispersed within a matrix, for example, a polymer matrix, improvements in release profiles are typically seen as a result of reduction in the particle size of the dispersed drug. In particular, particle size reduction can reduce the initial release or burst often associated with sustained release compositions. Therefore, it is often desirable to minimize and control the particle size of a drug.

SUMMARY OF THE INVENTION

The present invention relates to submicron particles of a biologically active agent and a method of preparing the submicron particles. The invention further relates to sustained release compositions comprising the submicron particles of biologically active agent described herein and to a method of preparing and administering the sustained release composition.

The method for preparing submicron particles of a biologically active agent comprises the steps of atomizing using multifluid atomization a dispersed system comprising at least one biologically active agent and at least one solvent at a mass flow ratio of about 0.30 or greater to produce droplets, freezing the droplets to produce frozen droplets, removing the solvent from the frozen droplets to produce friable microstructures, forming a dispersion of the friable miciostructures in at least one non-solvent for the biologically active agent and fragmenting the dispersed friable microstructures to produce submicron particles of the biologically active agent.

The submicron particles of a biologically active agent, as described herein, are prepared according to the method of the invention. The submicron particles of a biologically active agent are prepared by atomizing using multifluid atomization a dispersed system comprising at least one biologically active agent and at least one solvent at a mass flow ratio of about 0.30 or greater to produce droplets, freezing the droplets to produce frozen droplets, removing the solvent from the frozen droplets to produce friable microstructures, forming a dispersion of the friable microstructures in at least one non-solvent for the biologically active agent and fragmenting the dispersed friable microstructures to produce submicron particles of the biologically active agent.

The method of the invention for producing a composition for the sustained release of a biologically active agent comprises the steps of atomizing using multifluid atomization a dispersed system comprising at least one biologically active agent and at least one solvent at a mass flow ratio of about 0.30 or greater to produce droplets, freezing the droplets to produce frozen droplets, removing the solvent from the frozen droplets to produce friable microstructures, forming a dispersion of the friable microstructures in at least one non-solvent for the biologically active agent, fragmenting the dispersed friable microstructures to produce submicron particles of the biologically active agent, providing a suspension comprising the submicron particles of the biologically active agent, at least one biocompatible polymer and at least one polymer solvent and removing the polymer solvent to form a solid polymer/active agent matrix.

The composition for sustained release of a biologically active agent is likewise prepared according to the method of the invention. In other words, the composition for the sustained release of a biologically active agent as described herein is a composition prepared by the method comprising the steps of atomizing using multifluid atomization a dispersed system comprising at least one biologically active agent and at least one solvent at a mass flow ratio of about 0.30 or greater to produce droplets, freezing the droplets to produce frozen droplets, removing the solvent from the frozen droplets to produce friable microstructures, forming a dispersion of the friable microstructures in at least one non-solvent for the biologically active agent, fragmenting the dispersed friable microstructures to form submicron particles of the biologically active agent, providing a suspension comprising the submicron particles of biologically active agent, at least one biocompatible polymer, and at least one polymer solvent, and removing the polymer solvent to form a solid polymer/active agent matrix.

The sustained release composition of the present invention can be used in a method for providing a therapeutically, prophylactically, or diagnostically effective amount of a biologically active agent to a subject for a sustained period. The invention therefore also relates to a method for providing a therapeutically, prophylactically or diagnostically effective amount of a biologically active agent to a subject for a sustained period, comprising administering a dose of the sustained release composition prepared as described herein to a subject over a therapeutically useful period of time.

The invention has numerous advantages. For example, the submicron particles retain biological activity and are prepared with minimal agglomeration or aggregation. In addition, the submicron particles of biologically active agent, once formed, can, without isolation or additional comminution steps, be processed to form a composition for sustained release of the biologically active agent. The sustained release compositions, which are prepared according to the claimed method, exhibit a more favorable release profile than that observed with compositions having larger particles of biologically active agent incorporated therein. For example, the sustained release compositions having submicron particles show a decrease in the release of agent over the first twenty-four hours, and/or show an increase in the duration of sustained release, thereby possibly providing increased therapeutic benefits.

DETAILED DESCRIPTION OF THE INVENTION

Figure 1A:
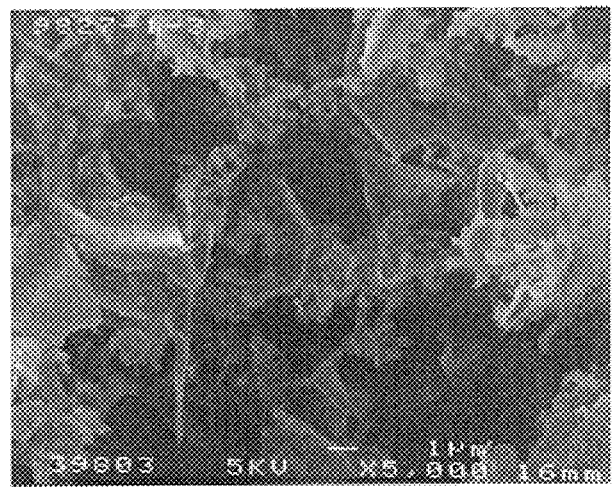
FIG. 1 shows scanning electron micrographs (SEMs) of friable microstructures of zinc-complexed recombinant human growth hormone (rhGH) prepared using A) a mass flow ratio of 0.14 (volume median particle size: 2.0 $\mu$m, drug powder batch 1); B) a mass flow ratio of 0.063 (volume median particle size : 4.5 $\mu$m, drug powder batch 3); and C) a mass flow ratio of 0.34 (volume median particle size: 0.45 $\mu$m, drug powder batch 5).
Figure 1B:
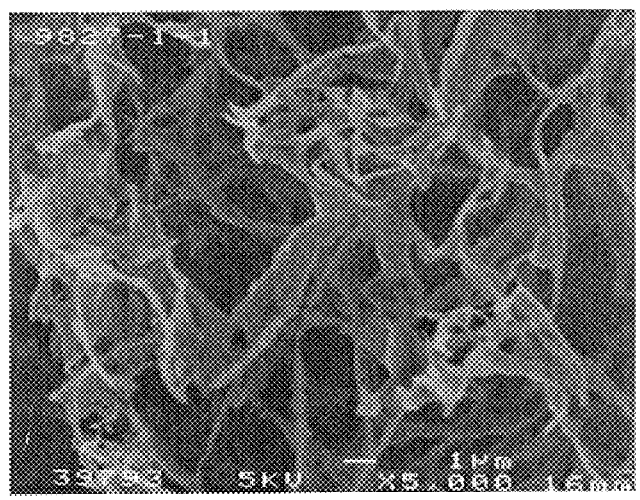
Figure 1C:
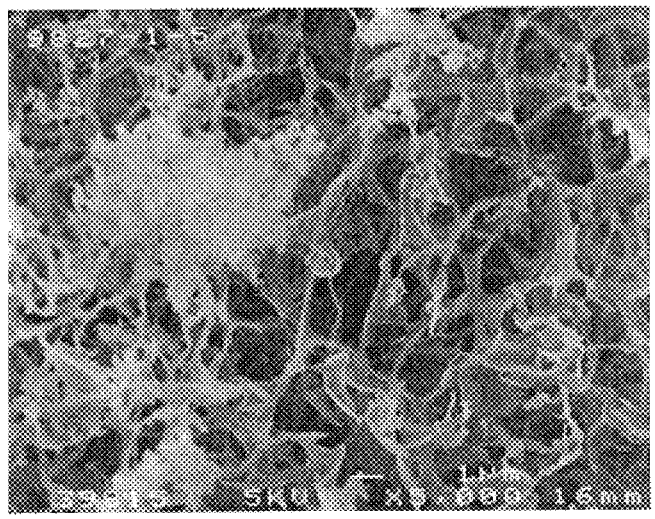
Figure 2:
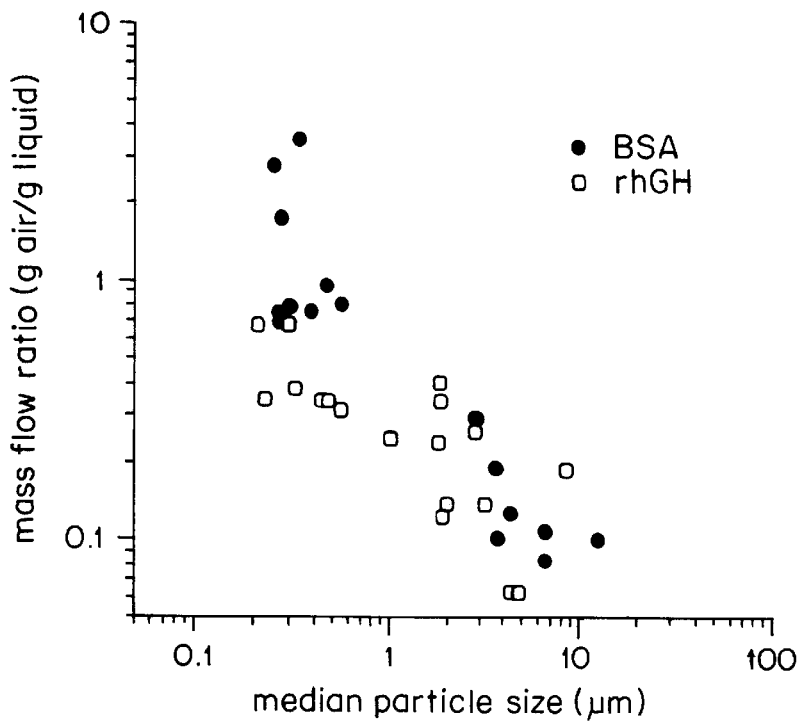
FIG. 2 is a graph of the mass flow ratio versus the volume median particle size ($\mu$m) of zinc-complexed rhGH and zinc-complexed BSA particles following sonication.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

The present invention relates to submicron particles of a biologically active agent and a method of preparing the submicron particles. The invention further relates to sustained release compositions comprising the submicron particles of biologically active agent prepared as described herein and to a method of preparing and administering the sustained release composition.

The method for preparing submicron particles of a biologically active agent comprises the steps of atomizing using multifluid atomization dispersed system comprising at least one biologically active agent and at least one solvent at a mass flow ratio of about 0.30 or greater to produce droplets, freezing the droplets to produce frozen droplets, removing the solvent from the frozer droplets to produce friable microstructures, forming a dispersion of the friable microstructures in at least one non-solvent for the biologically active agent and fragmenting the dispersed friable microstructures to produce submicron particles of the biologically active agent.

In practicing the method of the invention, the operating parameters for the multifluid atomization can be varied as described herein with the understanding that the conditions must result in a mass flow of about 0.30 or greater thereby providing a friable microstructure which upon fragmentation results in a submicron particle of the biologically active agent.

The submicron particles of a biologically active agent, as described herein, are prepared according to the method of the invention. The submicron particles of a biologically active agent are prepared by atomizing using multifluid atomization a dispersed system comprising at least one biologically active agent and at least one solvent at a mass flow ratio of about 0.30 or greater to produce droplets, freezing the droplets to produce frozen droplets, removing the solvent from the frozen droplets to produce friable microstructures, forming a dispersion of the friable microstructures in at least one non-solvent for the biologically active agent and fragmenting the dispersed friable microstructures to produce submicron particles of the biologically active agent.

The method of the invention for producing a composition for the sustained release of a biologically active agent comprises the steps of atomizing using multifluid atomization a dispersed system comprising at least one biologically active agent and at least one solvent at a mass flow ratio of about 0.30 or greater to produce droplets, freezing the droplets to produce frozen droplets, removing the solvent from the frozen droplets to produce friable microstructures, forming a dispersion of the friable microstructures in at least one non-solvent for the biologically active agent, fragmenting the dispersed friable microstructures to produce submicron particles of the biologically active agent, providing a suspension comprising the submicron particles of the biologically active agent, at least one biocompatible polymer and at least one polymer solvent and removing the polymer solvent to form a solid polymer/active agent matrix.

The method can further comprise the step of forming droplets of the suspension prior to removal of the polymer solvent. According to the method of the invention the droplets can be microdroplets. In a specific embodiment, wherein droplets are formed and then frozen, the polymer solvent can be removed by an evaporation or extraction process. Phase separation is also a suitable method.

The composition for sustained release of a biologically active agent is likewise prepared according to the method of the invention. In other words, the composition for the sustained release of a biologically active agent as described herein is a composition prepared by a method comprising the steps of atomizing using multifluid atomization a dispersed system comprising at least one biologically active agent and at least one solvent at a mass flow ratio of 0.3 or greater to produce droplets, freezing the droplets to produce frozen droplets, removing the solvent from the frozen droplets to produce friable microstructures, forming a dispersion of the friable microstructures in at least one non-solvent for the biologically active agent, fragmenting the dispersed friable microstructures to form submicron particles of the biologically active agent, providing a suspension comprising the submicron particles of biologically active agent, at least one biocompatible polymer, and at least one polymer solvent, and removing the polymer solvent to form a solid polymer/active agent matrix.

The sustained release composition of the present invention can be used in a method for providing a therapeutically, prophylactically, or diagnostically effective amount of a biologically active agent to a subject for a sustained period. The invention therefore also relates to a method for providing a therapeutically, prophylactically or diagnostically effective amount of a biologically active agent to a subject for a sustained period comprising administering a dose of the sustained release composition prepared as described herein to a subject over a therapeutically useful period of time.

As used herein, the term "particle size" refers to a volume median particle size as determined by conventional particle size measuring techniques known to those skilled in the art, such as, laser diffraction, photon correlation spectroscopy, sedimentation field flow fractionation, disk centrifugation or electrical sensing zone. Laser diffraction is preferred.

As used herein, the term "submicron particle" refers to particles having a volume median particle size of less than 1 micron (μm). The volume median particle size is the median diameter of the volume weighted size distribution, also referred to as $D_{V,50}$.

As used herein, the term "microparticles" refers to particles having a volume median particle size of between about 1 and 1000 microns.

As used herein, the term "dispersed system" refers to a suspension, a dispersion, a colloidal system or a solution of biologically active agent in a solvent. The solvent of the dispersed system can act to dissolve completely, partially or not substantially, the biologically active agent. The biologically active agent can be a stabilized biologically active agent as described herein. In addition, stabilizing agents and excipients can also be present in the dispersed system.

Water, aqueous buffers, organic solvents and mixtures thereof are suitable choices of solvents for use in the dispersed system. The choice of solvent can be determined for the particular biologically active agent being used and the type of dispersed system desired. A preferred solvent is a buffer, which can be either partially or completed removed. Buffers include, for example, ammonium salts, such as ammonium bicarbonate and sodium salts, such as sodium bicarbonate.

As used herein, the term "non-solvent" refers to a material which does not substantially dissolve a second or reference material.

Together the multifluid atomization and freezing steps of the method described herein, can be referred to as "spray freezing". Spray freezing of the dispersed system comprising at least one biologically active agent and at least one solvent can be carried out in an apparatus which includes a multifluid atomization nozzle assembly for multifluid atomizing of the dispersed system and a spray chamber. The dispersed system of biologically active agent in a solvent which is atomized can also be referred to as the "liquid feed".

The multifluid atomization assembly includes a spray head adapter into which the liquid feed and atomization gas are introduced through separate conduits. The atomization gas can be any gas which does not react with the dispersed system undergoing multifluid atomization. Examples of suitable atomization gasses include, but are not limited to, air, nitrogen, carbon dioxide, and argon. The atomization nozzle assembly also includes atomization a fluid cap and an air cap.

Examples of suitable multifluid atomization nozzles include, but are not limited to, external air (or gas) atomizers (e.g., Glatt Model 014 available from Ortho Liquid System, NC, Models SUE15A; SU2A and SU2 available from Spray Systems Co., Wheaton, Ill.), internal air atomizers (e.g., SU12; Spray Systems Co.) and pressure atomization nozzles (e.g., Type SSTC Whirl Jet Spray Drying Nozzles; Spray Systems Co., Wheaton, Ill.). The atomization nozzle can have an air cap with an inner diameter ranging from $64 \times 10^{-3}$ inch to $120 \times 10^{31\ 3}$ inch. Typicaly, a $70 \times 10^{-3}$ air cap is used.

Although multifluid atomization is preferred, single fluid atomization assemblies, for example, ultrasonic atomization, can be utilized provided that conditions which yield equivalent atomization energy and performance are employed.

The spray chamber is further provided with a conduit and nozzles for introduction of the freezing medium into the spray chamber. According to a preferred embodiment of the invention, the freezing medium is a cryogenic fluid, for example, liquid nitrogen or liquid argon. Accordingly, the apparatus for spray freezing is manufactured from materials and according to a design compatible with the temperatures of the process.

The liquid feed is atomized into droplets which freeze upon contact with the freezing medium. Frozen droplets are collected in a tank attached in some orientation to the spray chamber. Preferably the collection tank and the spray chamber are made of a material which can withstand the temperatures and gas pressures experienced in carrying out the process. A suitable material is, for example, stainless steel.

"Multifluid atomization" as that term is used herein refers to an atomization process which employs two fluids to achieve atomization. The two fluids can be, for example, a liquid and a gas.

The liquid flow rate (mL/min) can be calculated by determining the time needed to introduce a specified volume of liquid feed into the atomization nozzle assembly. The rate can also be determined by use of a flow meter, present in the system.

The atomization $N_2$ flow rate (L/min) as used herein is the flow rate under standard conditions of 0° C. and 760 mm of pressure. The flow rate can be determined using a gas flow meter. Suitable gas flow meters include, for example, a Compensated Differential Pressure Flow Meter such as Model 32915-72 available from Cole Parmer of Vernon Hills, Ill. The flow meter is typically located in-line upstream from the conduit through which the gas flows.

The friable microstructures of the invention are formed using the process described herein at a mass flow ratio of about 0.30 or greater. The mass flow ratio can range from about 0.3 to about 50, such as from about 0.3 to about 25 or about 0.3 to about 15. The employment of a mass flow ratio of about 0.30 or greater results in the formation of friable microstructures which upon fragmentation yield biologically active agent having a submicron particle size.

The mass flow ratio is defined as follows:

$$\frac{Q_{atomization\ gas}}{Q_{liquid\ feed}} = \frac{M_{atomization\ gas} \cdot \rho_{atomization\ gas}}{M_{liquid\ feed} \cdot \rho_{liquid\ feed}}$$

$Q_{atomization\ gas}$ = The mass flow rate for the atomization gas $Q_{liquid\ feed}$ = The mass flow rate for the liquid feed $M_{atomization\ gas}$ = The volumetric flow rate for the atomization gas $M_{liquid\ feed}$ = The volumetric flow rate for the liquid feed $\rho_{liquid\ feed}$ = The density of the liquid feed $\rho_{atomization\ gas}$ = The density of the atomization gas For purposes of the present invention, the density of the liquid feed was measured for each liquid feed processed by determining the mass of a given volume of the liquid feed. The density of the atomization gas, in all examples nitrogen, was the known density at standard conditions of $1.25 \times 10^{-3}$ g/cm$^3$.

The following example calculation is based on the process parameters used to achieve drug powder batch 4 of Table 1 having a $D_{V,50}$ of 0.45 μm.

$$0.34 = \frac{92\ \text{L/min} \times 1.25 \times 10^{-3}\ \text{g/cm}^3}{\left(339\ \text{mL/min} \times \dfrac{1\text{L}}{1000\ \text{mL}}\right) \times 1.00\ \text{g/cm}^3}$$

The total solids concentration of the liquid feed should be such that the friable microstructures do not become so dense as to inhibit formation of submicron particles following fragmentation. The liquid feed can further comprise other excipients which stabilize the active agent or modulate the release profile.

Figure 8:
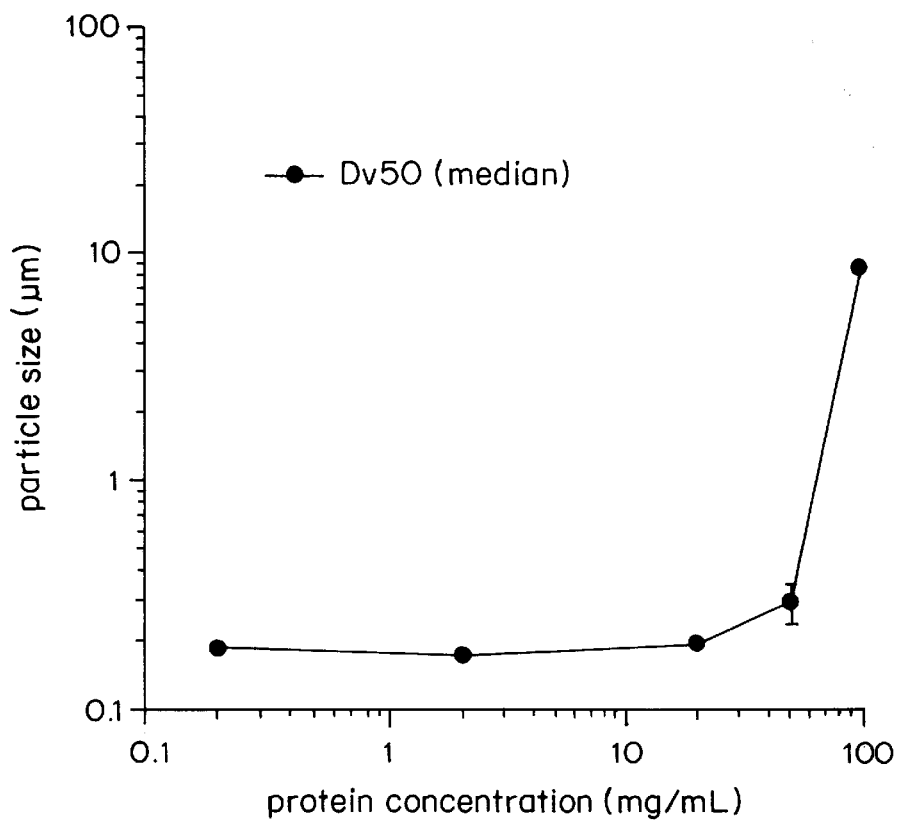
FIG. 8 is a graph of the volume median particle size of BSA drug powder following sonication versus protein concentration of the liquid feed (mg/mL).
Figure 9:
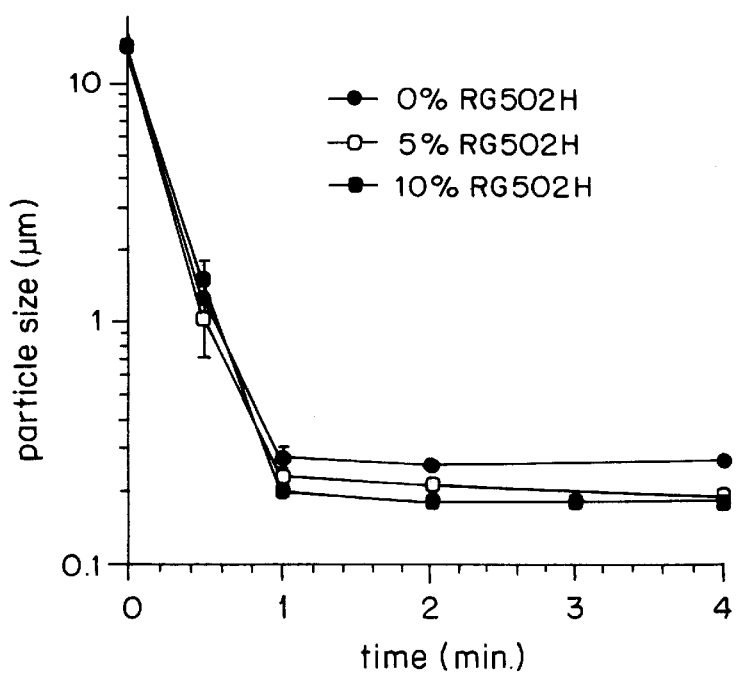
FIG. 9 is a graph of the particle size of dispersed friable microstructures of BSA in methylene chloride having varying concentrations of PLG versus time from onset of sonication.

FIG. 8 shows that protein concentration for a specific BSA liquid feed can be as high as 50 mg/mL in a 2.5 mM solution of sodium bicarbonate and still achieve a submicron particle size following the invention described herein. As such, the upper limit of concentration for any liquid feed can be determined by the same means as used to generate the graphed data shown in FIG. 8.

The solvent is removed from the frozen droplets by drying means known to those skilled in the art. For example, the solvent can be removed by lyophilization. In a preferred embodiment, the lyophilization cycle is designed to avoid nearing or exceeding the lowest $T_g$ of the components of the liquid droplets, thereby avoiding conditions where microstructures within the lyophilizate can grow, and in some instances result in larger particle sizes of the biologically active agent subsequent to fragmentation.

By carrying out the atomization, freezing and drying of the liquid feed, as described herein, the product obtained is in the form of friable microstructures. As used herein, the term "friable microstructures" refers to particulate biologically active agent capable of being fragmented into submicron particles by means and under conditions that do not deleteriously effect the activity of the biologically active agent. The friable microstructures have increased porosity, and specific surface area when compared to corresponding compositions prepared, using processing conditions yielding a mass flow ratio which is not in the desired range. The friable microstructures of biologically active agent can be referred to as a drug powder.

The friable microstructures prepared according to the claimed process possess a specific surface area which is larger than microstructures prepared from a corresponding liquid feed processed using conditions yielding a mass flow ratio which is not about 0.30 or greater. FIG. 7 shows graphically the direct relationship between the specific surface area of the friable microstructures measured using BET with nitrogen gas and the volume median particle size achieved following sonication. However, the absolute value of the specific surface area is dependent on the composition of the liquid feed. For example, FIG. 7 shows that the absolute value of the specific surface area is greater for friable microstructures of BSA drug powder which is excipient free, than for zinc-complexed BSA prepared under comparable process conditions.

The tap density of the friable microstructures of the invention, which represents a macroscale measure of the envelope mass density of particles, is less than or equal to 0.03 for the drug powder batches tested.

The friable microstructure is then dispersed in a non-solvent for the biologically active agent of the friable microstructure and fragmented to achieve submicron particles of biologically active agent. The choice of non-solvent is determined based on the dissolution characteristics of the biologically active agent of the friable microstructure. For example, if the biologically active agent is a protein, suitable non-solvents include, but are not limited to, methylene chloride, chloroform, acetone, ethyl acetate and tetrahydrofuran.

Fragmentation can be accomplished by means known to those skilled in the art, for example by probe sonication, homogenization, fluidization, comminution and milling. Fragmentation is performed under conditions and for a period of time which does not deleteriously effect the biological activity of the biologically active agent. In a preferred embodiment, fragmentation is conducted at a temperature which is lower than the lowest Tg of the components of the friable microstructure.

According to a preferred embodiment, fragmenting is conducted using probe sonication and results in particles referred to herein as "sonicated particles". Typical sonication times range from about 0.5 to about 5 minutes at microtip limit of the sonicator. The particle can also be fragmented using high pressure homogenization, for example, operating at about 10,000 psi with one or multiple passes.

In one embodiment, the non-solvent for the biologically active agent is a polymer solvent, thereby allowing, without isolation, further processing of the submicron particles into a polymer matrix to produce a sustained release composition. In another embodiment, the friable microstructures are dispersed in a non-solvent having a biocompatible polymer dissolved therein. FIG. 10 is a graph of particle size versus time for BSA drug power fragmented using sonication. The graph indicates that the submicron particles of drug powder are achieved following sonication of dispersions both with and without polymer.

The term "biologically active agent," as used herein, is an agent, or its pharmaceutically acceptable salt, which when released in vivo, possesses the desired biological activity, for example therapeutic, diagnostic and/or prophylactic properties in vivo. It is understood that the term includes stabilized biologically active agents as described herein.

Examples of suitable biologically active agents include proteins such as immunoglobulins, antibodies, cytokines (e.g., lymphokines, monokines, chemokines), interleukins, interferons, erythropoietin, nucleases, tumor necrosis factor, colony stimulating factors, insulin, enzymes (e.g. superoxide dismutase, a plasminogen activator), tumor suppressors, blood proteins, hormones and hormone analogs (e.g., growth hormone, adrenocorticotropic hormone, and luteinizing hormone releasing hormone (LHRH)), vaccines (e.g., tumoral, bacterial and viral antigens), antigens, blood coagulation factors; growth factors; peptides such as protein inhibitors, protein antagonists, and protein agonists; nucleic acids, such as antisense molecules; oligonucleotides; and ribozymes. Small molecular weight agents suitable for use in the invention include, antitumor agents such as bleomycin hydrochloride, carboplatin, methotrexate and adriamycin; antibiotics such as gentamicin, tetracycline hydrochloride and ampicillin; antipyretic, analgesic and anti-inflammatory agents; antitussives and expectorants such as ephedrine hydrochloride, methylephedrine hydrochloride, noscapine hydrochloride and codeine phosphate; sedatives such as chlorpromazine hydrochloride, prochlorperazine hydrochloride and atropine sulfate; muscle relaxants such as tubocurarine chloride; antiepileptics such as sodium phenytoin and ethosuximide; antiulcer agents such as metoclopramide; antidepressants such as clomipramine; antiallergic agents such as diphenhydramine; cardiotonics such as theophillol; antiarrhythmic agents such as propranolol hydrochloride; vasodilators such as diltiazem hydrochloride and bamethan sulfate; hypotensive diuretics such as pentolinium and ecarazine hydrochloride; antidiuretic agents such as metformin; anticoagulants such as sodium citrate and sodium heparin; hemostatic agents such as thrombin, menadione sodium bisulfite and acetomenaphthone; antituberculous agents such as isoniazide and ethanbutol; hormones such as prednisolone sodium phosphate and methimazole; antipsychotic agents such as risperidone; and narcotic antagonists such as nalorphine hydrochloride.

In one embodiment, the biologically active agent is stabilized. The biologically active agent can be stabilized against degradation, loss of potency and/or loss of biological activity, all of which can occur during formation of the submicron particles, during formation of the sustained release composition having the submicron particles dispersed therein, and/or prior to and during in vivo release of the biologically active agent. In one embodiment, stabilization can result in a decrease in the solubility of the biologically active agent, the consequence of which is a reduction in the initial release of biologically active agent, in particular, when release is from a sustained release composition. In addition, the period of release of the biologically active agent can be prolonged.

Stabilization of the biologically active agent can be accomplished, for example, by the use of a stabilizing agent. "Stabilizing agent", as that term is used herein, is any agent which binds or interacts in a covalent or non-covalent manner or is included with the biologically active agent. Stabilizing agents suitable for use in the invention are described in U.S. Pat. Nos. 5,716,644, 5,674,534, 5,654,010, 5,667,808, and 5,711,968, and co-pending U.S. patent applications Ser. No. 08/934,830 to Burke et al., filed on Sept. 22, 1997 and 09/104,549 to Burke, filed on Jun. 25, 1998 the entire teachings of which are incorporated herein by reference. For example, a metal cation can be complexed with the biologically active agent, or the biologically active agent can be complexed with a polycationic complexing agent such as protamine, albumin, spermidine and spermine, or associated with a "salting-out" salt.

Suitable metal cations include any metal cation capable of complexing with the biologically active agent. A metal cation-stabilized biologically active agent, as defined herein, comprises a biologically active agent and at least one type of metal cation wherein the cation is not significantly oxidizing to the biologically active agent. In a particular embodiment, the metal cation is multivalent, for example, having a valency of +2 or more. It is preferred that the metal cation be complexed to the biologically active agent.

Suitable stabilizing metal cations include biocompatible metal cations. A metal cation is biocompatible if the cation is non-toxic to the recipient, in the quantities used, and also presents no significant deleterious or untoward effects on the recipient's body, such as a significant immunological reaction at the injection site. The suitability of metal cations for stabilizing biologically active agents and the ratio of metal cation to biologically active agent needed can be determined by one of ordinary skill in the art by performing a variety of stability indicating techniques such as polyacrylamide gel electrophoresis, isoelectric focusing, reverse phase chromatography, and HPLC analysis on particles of metal cation-stabilized biologically active agents prior to and following particle size reduction and/or encapsulation. The molar ratio of metal cation to biologically active agent is typically between about 1:2 and about 100:1, preferably between about 2:1 and about 12:1.

Examples of stabilizing metal cations include, but are not limited to, $K^+$, $Zn+^2$, $Mg^{+2}$ and $Ca^{+2}$. Stabilizing metal cations also include cations of transition metals, such as $Cu^{+2}$. Combinations of metal cations can also be employed. In a particular embodiment, $Zn^{+2}$ is used as a stabilizing metal cation for rhGH at a zinc cation component to hGH molar ratio of about 4:1 to about 100:1. In a preferred embodiment, the zinc cation component to hGH molar ratio is about 4:1 to about 12:1, and most preferably 10:1.

The biologically active agent can also be stabilized with at least one polycationic complexing agent. Suitable polycationic complexing agents include, but are not limited to, protamine, spermine, spermidine and albumin. The suitability of polycationic complexing agents for stabilizing biologically active agents can be determined by one of ordinary skill in the art in the manner described above for stabilization with a metal cation. An equal weight ratio of polycationic complexing agent to biologically active agent is suitable.

The term "sustained release composition" as defined herein, comprises a polymer and submicron particles of a biologically active agent dispersed throughout the polymer (also referred to herein as a "polymer/biologically active agent matrix"). The polymers of the invention are biocompatible. Suitable biocompatible polymers, can be either biodegradable or non-biodegradable polymers or blends or copolymers thereof, as described herein.

A polymer, or polymer matrix, is biocompatible if the polymer, and any degradation products of the polymer, are substantially non-toxic to the recipient and also present no significant deleterious or untoward effects on the recipient's body, such as a significant immunological reaction at the site of administration.

Biodegradable, as defined herein, means the composition will degrade or erode in vivo to form smaller chemical species. Degradation can result, for example, by enzymatic, chemical and/or physical processes. Suitable biocompatible, biodegradable polymers include, for example, poly (lactides), poly(glycolides), poly(lactide-co-glycolides), poly(lactic acid)s, poly(glycolic acid)s, poly(lactic acid-co-glycolic acid)s, polycaprolactone, polycarbonates, polyesteramides, polyanhydrides, poly(amino acids), polyorthoesters, polyacetals, polycyanoacrylates, polyetheresters, poly(dioxanone)s, poly(alkylene alkylates) s, copolymers of polyethylene glycol and polyorthoester, biodegradable polyurethanes, blends and copolymers thereof.

Biocompatible, non-biodegradable polymers suitable for a sustained release device include non-biodegradable polymers selected from the group consisting of polyacrylates, polymers of ethylene-vinyl acetates and acyl substituted cellulose acetates, non-degradable polyurethanes, polystyrenes, polyvinyl chloride, polyvinyl fluoride, poly (vinyl imidazole), chlorosulphonate polyolefins, polyethylene oxide, blends and copolymers thereof.

Further, the terminal functionalities or pendant groups of the polymers can be modified, for example, to modify hydrophobicity, hydrophilicity and/or provide, remove or block moieties which can interact with the active agent (via, for example, ionic or hydrogen bonding).

Acceptable molecular weights for polymers used in this invention can be determined by a person of ordinary skill in the art taking into consideration factors such as the desired polymer degradation rate, physical properties such as mechanical strength, and rate of dissolution of polymer in solvent. Typically, an acceptable range of molecular weights is of about 2,000 Daltons to about 2,000,000 Daltons. In a preferred embodiment, the polymer is a biodegradable polymer or copolymer. In a more preferred embodiment, the polymer is a poly(lactide-co-glycolide) (hereinafter "PLG") with a lactide: glycolide ratio of about 1:1 and a molecular weight of about 5,000 Daltons to about 70,000 Daltons. In an even more preferred embodiment, the molecular weight of the PLG used in the present invention has a molecular weight of about 5,000 Daltons to about 42,000 Daltons.

The sustained release composition of this invention can be formed into many shapes such as a film, a pellet, a cylinder, a wafer, a disc or microparticles. A microparticle generally has a diameter of less than about one millimeter. Microparticles can have a generally spherical, non-spherical or irregular shape. Typically, the microparticle will be of a size suitable for injection. A preferred size range for microparticles is from about 1 to about 250 microns in diameter. The sustained release device in the form of a wafer or disc, for example, will typically be of a size suitable for implantation and, for example, can be manufactured by compressing microparticles.

As defined herein, a sustained release of biologically active agent which occurs over a period of time longer than that which would be obtained following direct administration. The sustained release of the present invention is also superior in that the initial release or burst of biologically active agent, typically seen with sustained release compositions is reduced. This reduction of the initial release or burst of biologically active agent in the sustained release composition of the present invention, is achieved by preparing the biologically active agent to be incorporated as submicron size particles. The release profile and amount of biologically active agent released can be affected by the loading of biologically active agent, selection of excipients to produce the desired effect and/or by other conditions such as the type of polymer used, the fabrication process employed and the ultimate geometry of the device. It is preferred that a sustained release be a release of biologically active agent which occurs over a period of greater than two days.

A sustained release composition of the invention can contain from about 0.01% (w/w) to about 90% (w/w) of active agent (dry weight of composition). The amount of agent can vary depending upon the desired effect of the agent, the planned release levels, and the time span over which the agent is to be released. A preferred range of agent loading is between about 0.1% (w/w) to about 30% (w/w). A more preferred range of agent loading is between about 0.5% (w/w) to about 20% (w/w) agent.

In another embodiment, the sustained release composition can contain excipients. These excipients are added to maintain the potency of the biologically active agent over the duration of release and modify polymer degradation. The excipients can be present in the dispersed system which is atomized or can be added following fragmentation of the friable microstructures. Suitable excipients include, for example, carbohydrates, amino acids, fatty acids, surfactants, salts and bulking agents, and are known to those skilled in the art. The amount of excipient used is based on ratio to the biologically active agent, on a weight basis. For amino acids, fatty acids, salts and carbohydrates, such as sucrose, lactose, mannitol, dextran and heparin, the ratio of carbohydrate to biologically active agent, is typically between about 1:10 and about 20:1. For surfactants, such as TWEEN® and PLURONIC® the ratio of surfactant to biologically active agent is typically between about 1:1000 and about 1:20.

Bulking agents typically comprise inert materials. Suitable bulking agents are known to those skilled in the art.

The excipient can also be a metal cation component which is not complexed to the biologically active agent. For example, in the case of a sustained release composition the metal cation component is dispersed within the polymer matrix. This metal cation component acts to modulate the release of the biologically active agent. The metal cation component can optionally contain the same species of metal cation, as is contained in the metal cation stabilized biologically active agent, and/or can contain one or more different species of metal cation. The metal cation component acts to modulate the release of the biologically active agent from the polymer matrix of the sustained release composition and can enhance the stability of the biologically active agent in the composition. A metal cation component used in modulating release typically comprises at least one type of multivalent metal cation. Examples of metal cation components suitable to modulate release include or contain, for example, $Mg(OH)_2$, $MgCO_3$ (such as $4MgCO_3 \cdot Mg(OH)_2 \cdot 5H_2O$), $MgSO_4$, $Zn(OAc)_2$, $Mg(OAc)_2$, $ZnCO_3$ (such as $3Zn(OH)_2 2ZnCO_3)ZnSO_4$, $ZnCl_2$, $MgCl_2$, $CaCO_3$, $Zn_3(C_6H_5O_7)_2$, and $Mg_3(C_6H_5O_7)_2$. A suitable ratio of metal cation component to polymer is between about 1:99 to about 1:2 by weight. The optimum ratio depends upon the polymer and the metal cation component utilized. A polymer matrix containing a dispersed metal cation component to modulate the release of a biologically active agent from the polymer matrix is further described in U.S. Pat. No. 5,656,297 to Bernstein et al. and co-pending U.S. patent application Ser. No. 09/056,566 filed on Apr. 7, 1998, the teachings of both of which are incorporated herein by reference in their entirety.

In yet another embodiment, at least one pore forining agent, such as a water soluble salt, sugar or amino acid, is included in the sustained release composition to modify the microstructure. The proportion of pore forming agent added to the suspension comprising submicron particles of biologically active agent dispersed in a solution comprising at least one biocompatible polymer and at least one polymer solvent, is between about 1% (w/w) to about 30% (w/w). It is preferred that at least one pore forming agent be included in a nonbiodegradable polymer matrix of the present invention.

Suitable methods for forming a composition for the sustained release of biologically active agent are described in U.S. Pat. No. 5,019,400, issued to Gombotz et al., and U.S. Pat. No. 5,912,253 issued to Herbert et al., the teachings of which are incorporated herein by reference in their entirety. This method of formation, as compared with other methods such as phase separation, can also reduce the amount of biologically active agent required to produce a sustained release composition with a specific biologically active agent content.

In this method, a suspension comprising submicron particles of the biologically active agent, dispersed in a solution comprising at least one biocompatible polymer and at least one polymer solvent, is processed to create droplets, wherein at least a significant portion of the droplets contains polymer, polymer solvent and the submicron particles of biologically active agent. The biologically active agent can be completely or partially insoluble in the polymer solution. According to one embodiment of the invention, the polymer solvent can be the same as the non-solvent for the biologically active agent employed in the fragmentation step. As such, isolation of the submicron particles is not necessary following fragmentation and the suspension of the submicron particles and the non-solvent can be combined with the biocompatible polymer and further processed.

The droplets are then frozen by a suitable means. Examples of means for processing the suspension to form droplets include directing the dispersion through an ultrasonic nozzle, pressure nozzle, Rayleigh jet, or by other known means for creating droplets from a solution.

Means suitable for freezing droplets include directing the droplets into or near a liquified gas, such as liquid argon or liquid nitrogen to form frozen microdroplets which are then separated from the liquid gas. The frozen microdroplets are then exposed to a liquid or solid non-solvent, such as ethanol, hexane, ethanol mixed with hexane, heptane, ethanol mixed with heptane, pentane or oil.

The solvent in the frozen microdroplets is extracted as a solid and/or liquid into the non-solvent to form a polymer/biologically active agent matrix comprising a biocompatible polymer and submicron particles of a biologically active agent. Mixing ethanol with other non-solvents, such as hexane, heptane or pentane, can increase the rate of solvent extraction, above that achieved by ethanol alone, from certain polymers, such as poly(lactide-co-glycolide) polymers.

A wide range of sizes of sustained release compositions can be made by varying the droplet size, for example, by changing the ultrasonic nozzle diameter. If the sustained release composition is in the form of microparticles, and very large microparticles are desired, the microparticles can be extruded, for example, through a syringe directly into the cold liquid. Increasing the viscosity of the polymer solution can also increase microparticle size. The size of the microparticles which can be produced by this process ranges, for example, from greater than about 1000 to about 1 micrometers in diameter.

The particles may be isolated from the extraction solvent by filtration and may be dried by evaporation to further remove the remaining solvent. The particles may be sized by passing them through an appropriate sized mesh.

Yet another method of forming a sustained release composition, from a suspension comprising a biocompatible polymer and submicron particles of a biologically active agent, includes film casting, such as in a mold, to form a film or a shape. For instance, after putting the suspension into a mold, the polymer solvent is then removed by means known in the art, or the temperature of the polymer suspension is reduced, until a film or shape, with a consistent dry weight, is obtained. Film casting of a polymer solution, is further described in U.S. Pat. No. 5,656,297, the teachings of which are incorporated herein by reference in their entirety.

Without being bound by a particular theory it is believed that the release of the biologically active agent can occur by two different mechanisms. First, the biologically active agent can be released by diffusion through aqueous filled channels generated in the polymer matrix, such as by the dissolution of the biologically active agent, or by voids created by the removal of the polymer solvent during the preparation of the sustained release composition. A second mechanism is the release of the biologically active agent, due to degradation of the polymer. The rate of degradation can be controlled by changing polymer properties that influence the rate of hydration of the polymer. These properties include, for instance, the ratio of different monomers, such as lactide and glycolide, comprising a polymer; the use of the L-isomer of a monomer instead of a racemic mixture; and the molecular weight of the polymer. These properties can affect hydrophilicity and crystallinity, which control the rate of hydration of the polymer. Hydrophilic excipients such as salts, carbohydrates, and surfactants can also be incorporated to increase hydration which can alter the rate of erosion of the polymer.

By altering the properties of the polymer, the contributions of diffusion and/or polymer degradation to biologically active agent release can be controlled. For example, increasing the glycolide content of a poly(lactide-co-glycolide) polymer and decreasing the molecular weight of the polymer can enhance the hydrolysis of the polymer and thus, provides an increased biologically active agent release from polymer erosion.

In addition, the rate of polymer hydrolysis is increased in non-neutral pH. Therefore, an acidic or a basic excipient can be added to the polymer suspension, used to form the sustained release composition, for example, microparticles, to alter the polymer erosion rate.

The composition of this invention can be administered in vivo, for example, to a human, or to an animal, by injection, implantation (e.g., subcutaneously, intramuscularly, intraperitoneally, intracranially, and intradermally), administration to mucosal membranes (e.g., intranasally, intravaginally, intrapulmonary, buccally or by means of a suppository), or in situ delivery (e.g., by enema or aerosol spray) to provide the desired dosage of biologically active agent based on the known parameters for treatment with the particular agent of the various medical conditions. As used herein, a "therapeutically effective amount", "prophylactically effective amount" or "diagnostically effective amount" is the amount of the submicron particles of biologically active agent or of the sustained release composition of biologically active agent needed to elicit the desired biological, prophylactic or diagnostic response following administration.

Even though the invention has been described with a certain degree of particularity, it is evident that many alternatives, modifications, and variations will be apparent to those skilled in the art in light of the foregoing disclosure. Accordingly, it is intended that all such alternatives, modifications, and variations which fall within the spirit and scope of the invention be embraced by the defined claims.

The invention will now be further and specifically described by the following examples which are not intended to be limiting.

EXEMPLIFICATIONS

EXAMPLE 1

Preparation and Characterization of Metal Cation-Complexed Recombinant Human Growth Hormone Drug Powder

COMPLEXATION

Metal cation-complexed rhGH drug powder batches 1–8 and 12–13 were prepared from bulk drug supplied as an aqueous solution of 6.18 mg/mL rhGH in 4 mM $NaHCO_3$, pH 8. The bulk drug was combined with a solution of zinc acetate (11.9 mM) at a 10:1 molar ratio of zinc to rhGH to yield a suspension of $Zn^{2+}$:rhGH (mol:mol) having a concentration of 5 mg/mL. All other batches listed in Table 1 were prepared from a bulk drug supplied as a solution of 23 mg/mL in 25 mM $NaHCO_3$, pH 8.4. The bulk drug at 23 mg/mL was combined with a solution of zinc acetate (69.7 mM) at a 10:1 molar ratio of zinc to rhGH to yield a suspension of $Zn^{2+}$:rhGH (mol:mol) having a concentration of 20 mg/mL. The concentration of each solution which was spray freeze dried is listed in Table 1.

SPRAY FREEZING

A solution containing the rhGH-zinc complex, prepared as detailed above, was atomized into a stainless steel chamber using a 2850 fluid cap with a 70 air cap. To freeze the liquid droplets, liquid $N_2$ was also sprayed in the chamber using 4×3004 nozzles.

The pressure on the liquid feed, atomization pressure, and concentration of the solution which was spray frozen were varied for each drug powder batch as indicated in Table 1. The liquid flow rate (mL/min) was determined as described above. The atomization $N_2$ flow rate (L/min) was measured using a gas flow meter, as earlier described. Employing process conditions as described in the preparation of drug powder batch 1 of Table 1, (atomization $N_2$ flow rate of 46 L/min, liquid flow rate of 418 mL/min) a mass flow ratio of 0.14 was achieved. This value is considered the control value for mass flow ratio in the experiments described herein.

Depending on the manner in which the sprayed and frozen biologically active agent is collected, in this example zinc-complexed rhGH, the process is described as an "open" or a closed process. In the closed process, the sprayed and frozen biologically active agent is collected in a stainless steel tank which is attached to the atomization chamber, thereby resulting in a closed system. The closed system is pressurized to about a 15 psi back pressure. In the open process, the sprayed and frozen agent is collected in a container which is positioned relative to the atomization chamber such that the system is open and pressurization to a predetermined back pressure is not possible.

Drug powder batches 16 and 18 were sprayed using a closed process. As such, the sprayed and frozen particles were collected in a stainless steel tank which was attached to the atomization chamber. All other batches listed in Table 1 were prepared using an open process, wherein the sprayed and frozen particles were collected in plastic containers.

DRYING OF PARTICLES

The collected particles were transferred into glass dishes, polyester bags or stainless steel pans suitable for use in lyophilization. The samples were loaded into a FTS Systems, Inc. (Durastopμp) lyophilizer. The lyophilization cycle used was a shelf temperature of 10° C. and a chamber pressure of 300 mTorr. Samples were loaded onto −40° C. pre-cooled shelves and lyophilized.

Sample 2 was subjected to an annealing step prior to lyophilization. Annealing was conducted by raising the shelf temperature to between −10 and −5° C. for about 1 hour (h) and then lowering to −40° C. prior to start of lyophilization.

CHARACTERIZATION OF ZINC-COMPLEXED rhGH DRUG POWDER PARTICLE SIZE

Particle size measurements of the drug powder were accomplished using a Coulter LS Particle Size Analyzer (Model 130) equipped with the Small Volume Module. The data was deconvoluted to obtain the particle size distribution using acetone as the circulating fluid and the analysis software supplied with the unit.

Particle size was determined after a four minute sonication in methylene chloride containing 10% (w/w) PLG at a 12.6% protein load in the polymer phase using a 3 mm microtip probe available from Sonics and Material, Danbury, Conn., and a Vibra Cell power supply at 20 kHz. $D_{V,50}$ is the volume median particle size. FIGS. 1A–1C and the particle size data in Table 1, show that zinc-complexed rhGH, prepared using process conditions resulting in a mass flow ratio of 0.14 (control) (drug powder batch 1), had a volume median particle size ($D_{V,50}$) of about 2 μm. In addition, drug powder batch 3 prepared using process conditions resulting in a mass flow ratio of 0.063 had a larger $D_{V,50}$ of about 4.5μm. However, drug powder batch 4 prepared using process conditions resulting in a mass flow ratio of 0.34 were submicron and had a $D_{V,50}$ of about 0.45 μm. FIG. 2 depicts the correlation between mass flow ratio and median particle size for batches found in Table 1.

The impact on particle size due to annealing of the sprayed and frozen zinc-complexed rhGH, as described above, was evaluated. The annealed sample (drug powder batch 2, of Table 1) showed an increased particle size when compared to a drug powder batch prepared using the same process conditions absent annealing (drug powder batch 1). However, submicron particles were obtained both with drug powder batches 1 and 2.

Drug powder batches 12–14 were prepared as described in Table 1. Drug powder batch 12 (control conditions) had a volume median particle size of 2.9 μm and was processed under conditions yielding a mass flow ratio of 0.26. Drug powder batch 13, which was processed under conditions yielding a mass flow of 0.25, exhibited a much lower volume median particle size of 1μm. Drug powder batch 14 had a particle size of 0.23 μm and was processed under conditions yielding a mass flow ratio of 0.35.

% MONOMERIC rhGH

The % monomer for the reconstituted protein was determined by size exclusion chromatography (SEC). SEC was conducted using a 7.8 μm ID×30 cm G2000SWXL TSK Gel column with a 5μm frit available from the Nest Group (Cat.#: 08540) and having a precolumn filter (Upchurch Scientific, Cat#: A314) with a 2μm frit (Upchurch Scientific, Cat.#: C-V3X). The flow rate was 1.0 mL/min with a column load of between 2.5 and 15 μg. The mobile phase consisted of sodium phosphate buffer 0.05 M $NaHl_2PO_4$, 0.15 M NaCl, pH 7.2±0.1. Detection was by UV absorption at 214 nm. The percent of total peak area (minus blank related peaks) that is associated with native monomeric hGH was calculated.

Drug powder batches 1, 3, 4, 17 and 18 were subjected to SEC to determine the % monomeric hGH. Prior to atomization, the bulk rhGH used to prepare the drug powder batches had a monomer content of 97.2±0.2%. The values of % monomeric rhGH listed in Table 1, indicate that the % of monomeric protein of the assayed drug powder batch was comparable to that of bulk rhGH. Therefore, a variance in the atomization conditions does not result in a loss of stability for the zinc-complexed rhGH.

SKELETAL DENSITY

Skeletal density was determined by helium pycnometery using a Quantachrome Micro-Ultrapycnometer 1000 (Boynton Beach, Fla.). Samples were stored in glass vials over desiccant in a vacuum dessicator at room temperature prior to testing. The sample amounts assayed were between 40 and 60 mgs. Measurements were performed at ambient temperatures. A total of three measurements were assayed for each sample.

SPECIFIC SURFACE AREA

The specific surface area of each sample was determined from nitrogen sorption data according to the Brunaucr, Emmett, and Teller (BET) equation. Nitrogen sorption experiments were performed on a Quantachrome NOVA 2000 surface area analyzer (Boynton Beach, Fla.). All samples were vacuum degassed at room temperature, overnight, prior to nitrogen sorption. Measurements were performed at 77° K and the specific surface area was determined in the BET region of the adsorption isotherm, between relative pressures of 0.05 to 0.3.

SCANNING ELECTRON MICROSCOPY

Scanning electron microscopy was conducted using a JEOL Model 6400 at a voltage of 5 kV. Samples were held in place with double-sided carbon tape affixed to an aluminum stub and sputter coated with a layer of gold. Photographs were taken at a magnification of 5000×. SEM of drug powder batches 1, 3 and 4 are presented in FIG. 1. Part (A) of FIG. 1 corresponds to drug powder batch 1 ($D_{V,50}$, 2.0 microns, mass flow ratio: 0.14), part (B) of FIG. 1 corresponds to drug powder batch 3 ($D_{V,50}$, 4.5 microns, mass flow ratio: 0.063), and part (C) of FIG. 1 corresponds to drug powder batch 4 ($D_{V,50}$, 0.45 microns, mass flow ratio: 0.34). The SEM data demonstrate a finer microstructure with increasing mass flow ratio.

The metal cation-complexed rhGH drug powder batches prepared as described above characterized in Table 1. The density of the 20 mg/mL solution was determined to be 1.00026 g/cm³. However, for purposes of determining the mass flow ratio using the equation presented herein, the density can be rounded to 1.00 g/cm³. The density of the 5 mg/mL solution was approximated at 1.00 for determination of the mass flow ratio. The difference in density between the two liquid feeds is such that the 1.00 g/cm³ for both is acceptable.

Extracting the polymer solvent from the frozen droplets into an extraction solvent (e.g., ⁻80° C. ethanol), thereby forming a polymer/biologically active agent matrix (e.g., microparticles).

Separating the matrix from the extraction solvent by filtration.

Removing any remaining solvent from the matrix.

Sieving of the product by passage through an appropriately sized mesh.

TABLE 1

Characterization of rhGH Drug Powder

| Drug Powder Batch | Liq. Vol mL | Protein Conc. (mg/mL) | Atom. $N_2$ Pressure (psi) | Atom. $N_2$ Flow rate (L/min) | Liquid Pressure (psi) | Liquid Flow rate (mL/min) | $D_{v,50}$ ($\mu$m) | Mass Flow Ratio | Monomeric rhGH (%) |
|---|---|---|---|---|---|---|---|---|---|
| 1 | 80 | 5 | 30 | 46 | 30 | 418 | 2.0 | 0.14 | 97.5 ± 0.1 |
| 2 | 80 | 5 | 30 | 46 | 30 | 418 | 3.2 | 0.14 | 97.5 ± 0.1 |
| 3 | 80 | 5 | 10 | 24 | 30 | 474 | 4.5 | 0.063 | 97.4 ± 0.1 |
| 4 | 80 | 5 | 80 | 92 | 30 | 339 | 0.45 | 0.34 | 97.5 ± 0.1 |
| 5 | 80 | 5 | 32 | 46 | 30 | 470 | 1.9 | 0.12 | nd[c] |
| 6 | 80 | 5 | 105 | 120 | 30 | 480 | 0.55 | 0.31 | nd |
| 7 | 80 | 5 | 52 | 70 | 30 | 466 | 8.4 | 0.19 | nd |
| 8 | 65 | 5 | 74 | 92 | 15 | 336 | 1.8 | 0.34 | nd |
| 9 | 75 | 20 | 79 | 92 | 30 | clog[b] | 0.32 | nd | nd |
| 10 | 30 | 20 | 82 | 82 | 30 | 436 | 1.8 | 0.24 | nd |
| 11 | 30 | 20 | 104 | 120 | 30 | 373 | 1.8 | 0.40 | nd |
| 12 | 80 | 5 | 28 | 46 | 30 | 218 | 2.9 | 0.26 | nd |
| 13 | 80 | 5 | 73 | 92–97 | 30 | 480 | 1.03 | 0.25 | nd |
| 14 | 80 | 20 | 100 | 121 | 3 | 436 | 0.23 | 0.35 | nd |
| 15 | 40 | 20 | 90 | 121 | 3 | 400 | 0.32 | 0.38 | nd |
| 16[c] | 300 | 20 | 100 | 120 | 22 | 225 | 0.21 | 0.67 | nd |
| 17 | 248 | 20 | 120 | 88–108 | 3 | clog | 0.24 | nd | 99.5 ± 0.1 |
| 18[c] | 100 | 21 | 100 | 120 | 22 | 217 | 0.30 | 0.69 | 99.6 ± 0.1 | nd = not determined.
[a]The resulting drug powder was in the form of a collapsed powder.
[b]The liquid flow was reduced due to a clogged liquid nozzle.
[c]On-line atomization with 15 psi back pressure.

The data in Table 1 show that, in general, process conditions which result in a mass flow ratio of about 0.30 or greater provide friable microstructures, which upon sonication, result in a drug powder with a submicron particle size.

EXAMPLE 2

Preparation and Characterization of Sustained Release Compositions Containing Submicron Particles of Zinc-Complexed rhGH

POLYMER

The polymer employed in the examples of Table 2 is described below:

RG 502H: 50:50 poly(D,L-lactide-co-glycolide) (PLG) with hydrophilic end groups, nominal MW 10k Daltons purchased from Boehringer Ingelheim Chemicals, Inc. of Montvale, N.J.

GENERAL PROCESS FOR THE PREPARATION OF SUSTAINED RELEASE COMPOSITIONS CONTAINING SUBMICRON PARTICLES OF rhGH

Forming droplets of a suspension comprising submicron particles of at least one biologically active agent dispersed in a solution of at least one biocompatible polymer, at least one polymer solvent and any excipients by atomizing the suspension.

Freezing the droplets by contact with a cryogenic liquid (e.g., liquid nitrogen).

The sustained release compositions containing drug powder comprising zinc-complexed rhGH described herein, are also referred to as "Encapsulated Drug Substances" (EDS) or microparticles. EDS batches 19, 20, 21 and 25 listed in Table 2, were prepared using an amount of zinc-complexed rhGH sufficient to achieve a theoretical protein load of 12.6%. $ZnCO_3$ sufficient for a theoretical total zinc load of 4.4% (7.8% theoretical $ZnCO_3$ load) was also present. All other EDS samples listed in Table 2, were prepared to achieve a theoretical protein load (in the microparticles) of 16.5% and a theoretical total zinc load of 1.0% (1.0% theoretical $ZnCO_3$ load).

The EDS batches listed in Table 2 were prepared as follows. Zinc-complexed drug powder was suspended in methylene chloride containing 10% (w/v) PLG. $ZnCO_3$ sufficient to achieve the listed theoretical zinc load was added. The suspension was sonicated for four minutes with a tapered microtip while being cooled in an ice bath. Atomization was carried out using a sonication nozzle (at 20% power). The droplets resulting from atomization were frozen by contact with liquid nitrogen. The frozen droplets were collected in a plastic dish containing a bed of 40×volume of frozen ethanol layered with liquid $N_2$. The plastic dish and contents were incubated at about 80° C. to allow for extraction of methylene chloride into the ethanol phase, also referred to as curing. After overnight storage, another 40×volume of cold ethanol (about −80° C.) was added and curing was allowed to progress for another 2 days at about −80° C. Following curing, polymer microparticles were harvested by cold-filtration and placed on a pre-cooled (about −40° C.) lyophilizer shelf. For a typical cycle, the chamber pressure was lowered to about 10 mTorr and the shelf temperature was raised in a series of steps from about −40 to about −5° C., then to about +10° C, and finally to about +15° C. (total cycle time was four days).

Particle size measurements of the isolated microparticles were conducted using a Coulter LS Particle Size Analyzer (Model 130) equipped with the Small Volume Module using water as the circulating fluid. The data was deconvoluted to obtain the particle size distribution using the analysis software supplied with the unit. All scanning electron microscopy (SEM) was conducted at a voltage of 5 kV and photographs were taken at a magnification of 5000× using a JEOL Model 6400.

IN VITRO RELEASE

In vitro release of rhGH from microparticles containing zinc-complexed rhGH, prepared as described above and characterized in Table 2 below, was determined as follows. Microparticles (10 mg) were suspended in 1.0 mL of buffer (50mM HEPES, 85 mM KCl, 0.01% NaN$_3$, pH 7.2) and incubated at 37° C. for a period of 18 h. Following incubation, the supernatant was removed and the amount of protein released was quantified using the BioRad Protein Assay (BioRad, Inc. Richmond, Calif.).

Figure 3:
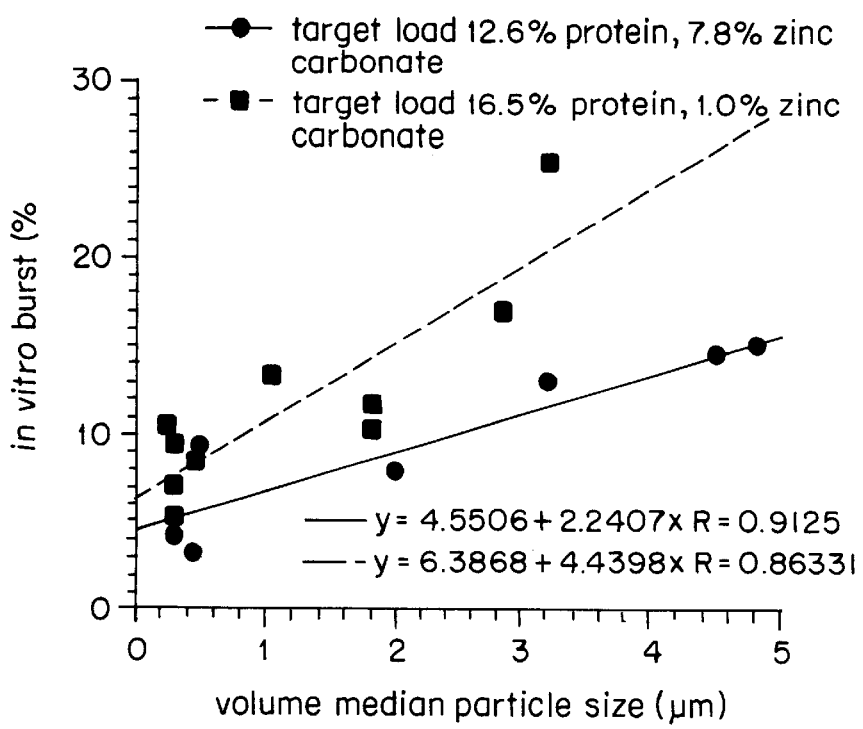
FIG. 3 is a graph of % in vitro burst of rhGH from microparticles containing zinc-complexed rhGH versus the volume median particle size of the encapsulated zinc-complexed rhGH particles.

FIG. 3 shows the correlation between the particle size of zinc-complexed rhGH drug powder following sonication, and the in vitro initial release of rhGH from microparticles containing the zinc-complexed rhGH drug powder. The data show that a reduction in the volume median particle size of the zinc-complexed rhGH drug powder results in a reduction in the initial release of rhGH from the microparticles. In addition the data shows that for a given drug powder particle size, the microparticles with lower protein load (12.5%) had a lower in vitro initial release than the microparticles with a higer load (16.5%). Typically, levels of initial release range from 24–39% for microparticles containing zinc-complexed rhGH prepared using, control conditions as described above. However, the microparticles listed in Table 2, which contain zinc-complexed rhGH drug powder having a volume median particle size in the submicron range, show an in vitro initial release of between about 5 and 10%.

TABLE 2

Characterization of rhGH Encapsulated Drug Substance

| EDS batch | Drug Powder batch | Protein Load (%) [th. %] | Zn load (%) [th. % Zn] <th. % ZnCO$_3$> | Drug Powder Particle Size (D$_{v,50}$) | EDS size (μm) | In vitro initial release (%) |
|---|---|---|---|---|---|---|
| 19 | 1 | 12.5 [12.6] | 3.36 [4.4] <7.8> | 2.0 | 64 | 7.8 |
| 20 | 3 | 12.8 [12.6] | 3.12 [4.4] <7.8> | 4.5 | 72 | 14.5 |
| 21 | 4 | 12.3 [12.6] | 3.48 [4.4] <7.8> | 0.45 | 62 | 3.3 |
| 22 | 9 | 16.5 [16.5] | 0.64 [1.0] <1.0> | 0.32 | 58 | 9.4 |
| 23 | 10 | 16.1 [16.5] | 0.86 [1.0] <1.0> | 1.8 | 62 | 11.7 |
| 24 | 11 | 16.2 [16.5] | 0.70 [1.0] <1.0> | 1.8 | 64 | 10.2 |
| 25 | 9 | 13.3 [12.6] | 3.43 [4.4] <7.8> | 0.32 | 66 | 4.2 |
| 26 | 9 | 16.3 [16.5] | 0.88 [1.0] <1.0> | 0.32 | 110 | 5.3 |
| 27 | 4 | 11.5 [16.5] | 0.99 [1.0] <1.0> | 0.45 | 79 | 8.5 |
| 28 | 2 | 16.6 [16.5] | 0.84 [1.0] <1.0> | 3.2 | 51 | 25.5 |
| 29 | 12 | 16.6 [16.5] | 1.16 [1.0] <7.8> | 2.9 | 84 | 16.9 |
| 30 | 13 | 16.6 [16.5] | 1.10 [1.0] <7.8> | 1.03 | 110 | 13.3 |
| 31 | 14 | 16.6 [16.5] | 1.09 [1.0] <7.8> | 0.23 | 84 | 10.4 |
| 32 | 15 | 16.6 [16.5] | 1.01 [1.0] <1.0> | 0.32 | 98 | 7.1 |

IN VIVO RELEASE

In vivo release studies of rhGH EDS were conducted in male Sprague-Dawley rats. The study consisted of eight treatment groups (A–H) with three subjects per treatment group. The Treatment Groups are described as follows: A) 50 mg of EDS batch 22; B) 50 mg of EDS batch 23; C) 50 mg of EDS batch 19; D) 50 mg of EDS batch 21; E) 50 mg of EDS batch 31; F) 50 mg of EDS batch 25; G) 50 mg of EDS batch 28; and H) 50 mg of EDS batch 24. The micropaiticles (approximately 50 mg) were suspended in aqueous vehicle comprising 3% carboxymethylcellulose (CMC) low viscosity, 0.1% Tween 20, in 0.9% NaCl and subcutaneously injected in the mid-scapula region into each member of the treatment group. Blood samples were withdrawn from the lateral tail vein at pre-dose, and after administration at 2, 4, 6, 10 and 24 hours and 2, 4, 7, 10, 14, 17, 21, 24 and 28 days. Plasma fractions were analyzed by an ELISA provided in an hGH kit available from Boehringer Mannheim (Catalog No.: 15868). The maximum plasma rhGH concentration ($C_{max}$) and the total area under-the-curve up to 1 day post-injection ($AUC_{0-1\ day}$) were calculated.

Table 3 describes Treatment Groups A–H and summarizes the results of the in vivo study. Specifically, the highest serum concentration recorded ($C_{max}$) and the total area under-the-curve up to 1 day post-injection ($AUC_{0-1\ day}$) for Treatment Groups A–H are presented.

TABLE 3

In Vivo Study

| Treatment Group | EDS rhGH load (%) [EDS batch] | Drug powder particle size ($\mu$m) [batch #] | $C_{max}$ (ng/mL) | $AUC_{0-1\ day}$ (ng · d/mL) |
|---|---|---|---|---|
| A | 16.5 [22] | 0.32 [9] | 304 ± 49 | 155 ± 27 |
| B | 16.1 [23] | 1.8 [10] | 399 ± 75 | 189 ± 45 |
| C | 12.5 [19] | 2.0 [1] | 605 ± 193 | 273 ± 77 |
| D | 12.3 [21] | 0.45 [4] | 209 ± 78 | 120 ± 27 |
| E | 16.6 [31] | 0.23 [14] | 454 ± 58 | 274 ± 37 |
| F | 13.3 [25] | 0.32 [9] | 185 ± 7 | 106 ± 9 |
| G | 16.6 [28] | 3.2 [2] | 1130 ± 409 | 579 ± 179 |
| H | 16.2 [24] | 1.8 [11] | 458 ± 111 | 191 ± 46 |

Figure 4:
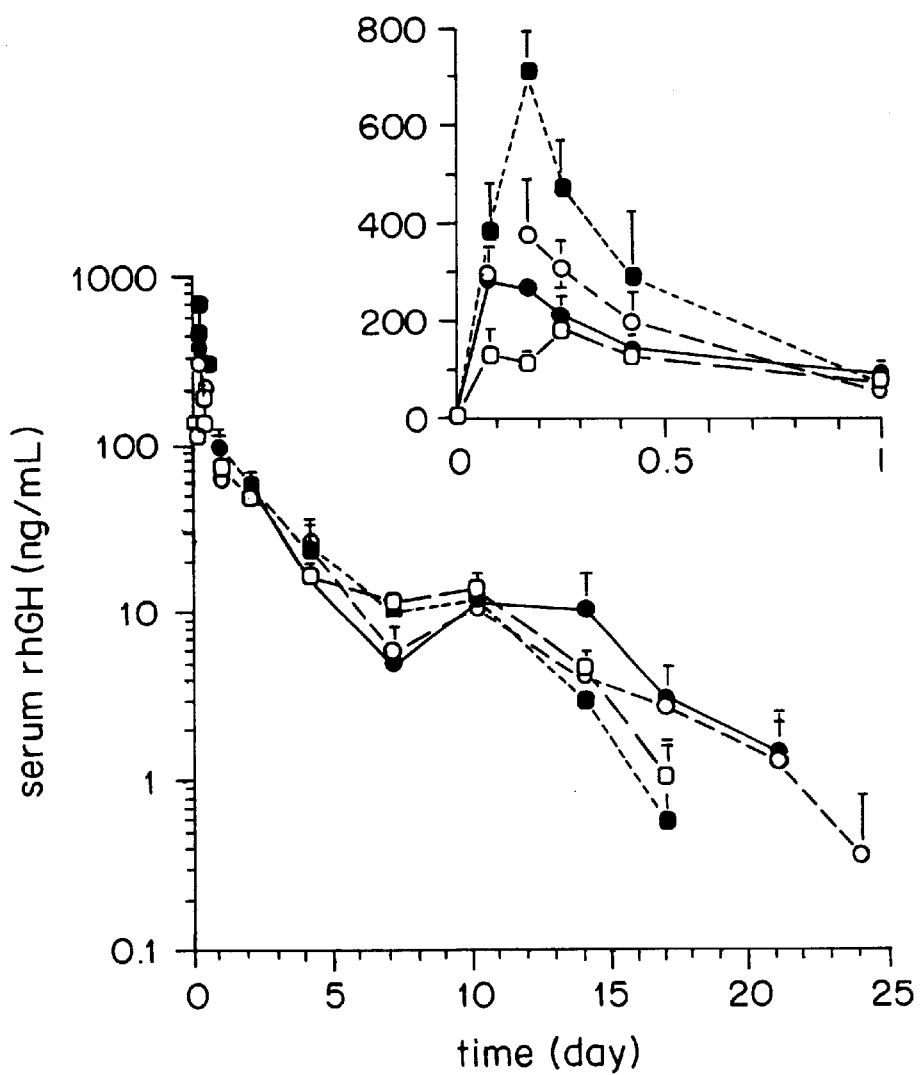
FIG. 4 is a plot of the serum concentration (ng/mL) of rhGH versus time following administration of microparticles containing zinc-complexed rhGH to immunosuppressed Sprague-Dawley rats.
Figure 5:
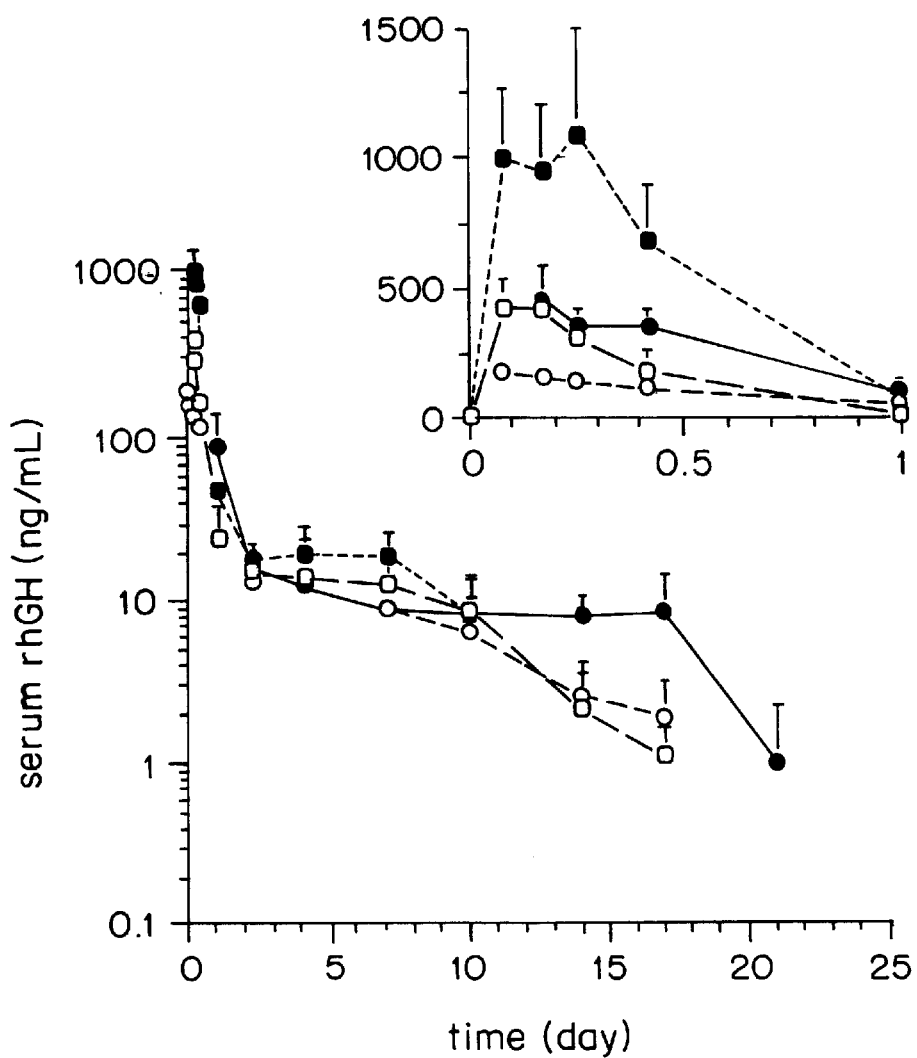
FIG. 5 is a plot of the serum concentration (ng/mL) of rhGH versus time following administration of microparticles containing zinc-complexed rhGH.
Figure 6:
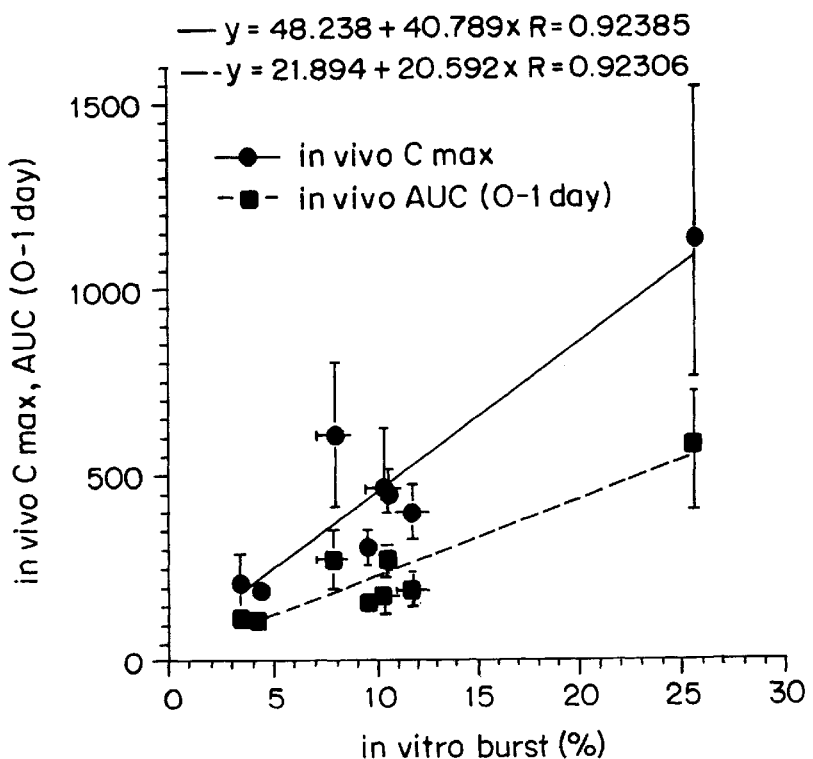
FIG. 6 shows the correlation between in vivo and in vitro release of rhGH from microparticles containing zinc-complexed rhGH for both in vivo Cmax and in vivo area under the curve (AUC) from 0–1 day.
Figure 7:
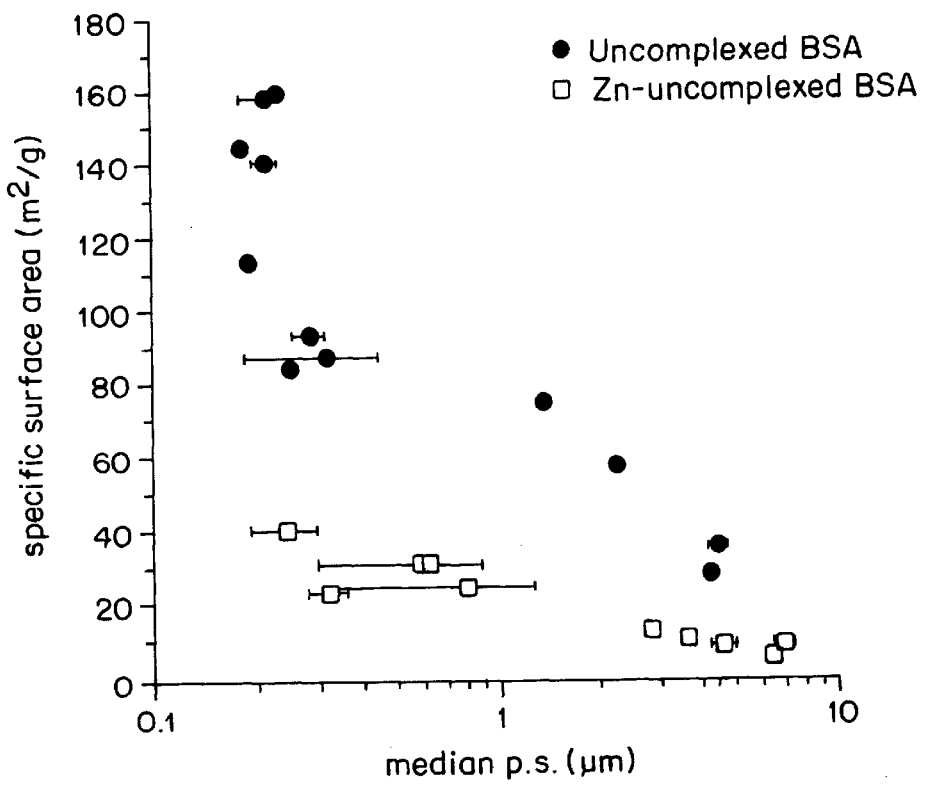
FIG. 7 is a graph of the specific surface area of spray freeze dried drug powders of zinc-complexed BSA and BSA versus volume median particle size following sonication of the spray freeze dried drug powders in methylene chloride.

For Treatment Groups A–D, two EDS samples were chosen at each target protein load. One of the two contained submicron sized zinc-complexed rhGH drug powder and the other contained zinc-complexed rhGH drug powder having a particle size of about 2 $\mu$m. FIG. 4 depicts the serum concentration of rhGH (ng/mL) for Treatment Groups A–D. It is apparent from FIG. 4 that, $C_{max}$ and $AUC_{0-1\ day}$ are less for treatment groups receiving EDS batches having incorporated therein a drug powder with a submicron particle size (Groups A and D).

For example, for a target protein load of 12.6%. the rhGH EDS produced from a 0.45-micron sized drug powder (EDS batch 21) had a ($C_{max}$ of 209 ng/mL and an $AUC_{0-1\ day}$ of 120 ng·day/mL. However, EDS batch 19 prepared at the same target load but using a 2.0-micron sized drug powder (drug powder batch 1) had a $C_{max}$ of 605 ng/mL and an $AUC_{0\text{-}1\ day}$ day of 273 ng·day/mL.

For Treatment Groups E–H, three of the four EDS samples administered had high target protein loads with the remaining EDS having a lower target protein load. The high load EDS batches were prepared from drug powder batches having volume median particle sizes of 0.23, 1.8 and 3.2 microns. The lower load EDS batch was prepared using a drug powder having a volume median particle size of 0.23 microns.

FIG. 5 depicts the serum concentration of rhGH (ng/mL) for Treatment Groups E–H. It is apparent from FIG. 5 that, $C_{max}$ and $AUC_{0\text{-}1\ day}$ day are less when the volume median particle size of the LDS used to prepare the EDS is reduced. In addition, animals that were administered microparticles exhibiting a relatively high initial release (EDS Batch 28) did not have measurable levels of rhGH in their sera after day 10, whereas a longer duration of release was observed for the other treatment groups. For example, Treatment Group E which was administered EDS Batch 31, showed an average serum rhGH concentration of about 1 ng/mL 21 days after injection.

Thus, the in vivo studies corroborated the results seen in vitro, wherein a reduction in the particle size of the drug powder which is incorporated, results in reduction of the initial release of drug from the microparticles. FIG. 6 shows the correlation for both in vivo $C_{max}$ (ng/mL) and $AUC_{0\text{-}1\ day}$ (ng·d/mL) in relation to the corresponding in vitro initial release The correlation for both $C_{max}$ and $AUC_{0\text{-}1\ day}$ day with the initial in vitro release data was determined to be greater than 0.92.

EXAMPLE 3

Preparation and Characterization of Submicron Particles of Zinc-Complexed Bovine Serum Albumin (BSA)

The data presented in Tables 4 and 5 were generated using methods and techniques earlier described for rhGH. The conditions and equipment were varied as noted in the tables employing the process described above for rhGH. The dispersed system comprised 20 mg/mL BSA in 25 mM sodium bicarbonate complexed with zinc. The density (ρ) of the liquid feed was determined to be 0.9992 g/cm$^3$. However, for the purpose of calculating the mass flow ratio a value of 1.00 g/cm$^3$ for the density is acceptable.

Tap density, specific surface area and skeletal density measurements were taken for samples prepared using the atomization conditions tabulated in Table 4. Table 5 presents characteristics of the drug powder batches prepared according to the conditions described in Table 4. FIG. 7 is a plot of the specific surface area versus the median particle size fo the zinc-complexed BSA (open symbols).

TABLE 4

20 mg/mL Zinc-Complexed BSA

| Atomization Condition | Drug Powder Batch # | Air Cap | Nozzle | Liquid Pressure (psi) | Liquid Flow Rate mL/min | Atomization $N_2$ Pressure (psi) | Atomization $N_2$ Flow Rate (L/min) | Median Particle Size $D_{v,50}$ (μm) |
|---|---|---|---|---|---|---|---|---|
| 1 | 33 | 64 | 2050 | 3 | 33 | 20 | 20 | 0.38 |
| 2 | 34 | 70 | 2850 | 30 | 568 | 40 | 38 | 6.6 |
| 3 | 35 | 120 | 1650 | 120 | 198 | 2 | 20 | 4.3 |
| 4 | 36 | 64 | 1650 | 30 | 129 | 120 | 70 | 0.28 |
| 5 | 37 | 70 | 2050 | 120 | 498 | 82 | 100 | 2.8 |
| 6 | 38 | 120 | 2850 | 3 | 131 | 18 | 100 | 0.47 |
| 7 | 39 | 64 | 2850 | 102 | 857 | 102 | 74 | 6.6 |
| 8 | 40 | 70 | 1650 | 3 | 58 | 130 | 130 | 0.26 |
| 9 | 41 | 120 | 2050 | 30 | 217 | 26 | 140 | 0.56 |
| 10 | 42 | 64 | 1650 | 110 | 244 | 23 | 64 | 3.7 |

TABLE 4-continued 20 mg/mL Zinc-Complexed BSA

| Atomization Condition | Drug Powder Batch # | Air Cap | Nozzle | Liquid Pressure (psi) | Liquid Flow Rate mL/min | Atomization N₂ Pressure (psi) | Atomization N₂ Flow Rate (L/min) | Median Particle Size D$ TABLE 6-continued 20 mg/mL BSA

| Atomization Condition | Drug Powder Batch # | Air Cap | Nozzle | Liquid Pressure (psi) | Liquid Flow Rate (mL/min) | Atomization N$_2$ Pressure (psi) | Median Particle Size D$_{v,50}$ ($\mu$m) |
|---|---|---|---|---|---|---|---|
| 10 | 61 | 64 | 1650 | 110 | 168 | 18 | 4.2 |
| 11 | 62 | 70 | 2050 | 5 | nd | 6 | 1.1 |
| 12 | 63 | 120 | 2850 | 30 | nd | 2 | 8.3 |
| 13 | 64 | 64 | 2850 | 3 | 211 | 118 | 0.30 |
| 14 | 65 | 70 | 1650 | 30 | 133 | 32 | 0.27 |
| 15 | 66 | 120 | 2050 | 118 | 441 | 12 | 4.2 |
| 16 | 67 | 64 | 2050 | 30 | 224 | 120 | 1.3 |
| 17 | 68 | 70 | 2850 | 120 | 882 | 112 | 4.2 |
| 18 | 69 | 120 | 1650 | 6 | 84 | 28 | 0.20 |
| 19 | 70 | 70 | 2850 | 3 | 197 | 92 | 0.30 |
| 20 | 71 | 120 | 2850 | 3 | 109 | 88 | 0.22 |
| 21 | 72 | 120 | 2850 | 3 | 137 | 84 | 0.19 |

Liquid Nitrogen Pressure in the spray chamber ranged from 22–45 psi for the atomization conditions tested.
nd = not determined

TABLE 7

20 mg/mL BSA

| Drug Powder Batch # | Atomization Condition | Median Particle Size D$_{V,50}$ ($\mu$m) | Tap Density (g/mL) | Specific Surface Area (m$^2$/g) | Skeletal Density (gm/cc) |
|---|---|---|---|---|---|
| 52 | 1 | 1.4 | 0.011 | nd | nd |
| 53 | 2 | 4.2 | 0.014 | nd | nd |
| 54 | 3 | 5.9 | 0.014 | nd | nd |
| 55 | 4 | 0.18 | 0.013 | 113 | 0.95 |
| 56 | 5 | 2.3 | 0.011 | 58.4 | 0.90 |
| 57 | 6 | 0.31 | 0.011 | 160 | 1.01 |
| 58 | 7 | 5.3 | 0.016 | nd | nd |
| 59 | 8 | 0.18 | 0.014 | 145 | 0.92 |
| 60 | 9 | 0.25 | 0.011 | 84.4 | 1.10 |
| 61 | 10 | 4.2 | 0.012 | 28.1 | 1.01 |
| 62 | 11 | 1.1 | 0.012 | nd | nd |
| 63 | 12 | 8.3 | 0.015 | nd | nd |
| 64 | 13 | 0.30 | 0.011 | 93.6 | 0.85 |
| 65 | 14 | 0.27 | 0.010 | nd | nd |
| 66 | 15 | 4.2 | 0.011 | nd | nd |
| 67 | 16 | 1.3 | 0.014 | 75.3 | 0.96 |
| 68 | 17 | 4.2 | 0.013 | 36.0 | 0.90 |
| 69 | 18 | 0.20 | 0.012 | nd | nd |
| 70 | 19 | 0.30 | 0.011 | 87.6 | nd |
| 71 | 20 | 0.22 | 0.016 | 140 | 1.09 |
| 72 | 21 | 0.19 | 0.015 | 158 | 0.86 | nd = not determined

EQUIVALENTS

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. A method for preparing submicron particles of a biologically active agent comprising the steps of:
    (a) atomizing using multifluid atomization a dispersed system comprising at least one biologically active agent and at least one solvent at a mass flow ratio of about 0.30 or greater to produce droplets;
    (b) freezing the droplets to produce frozen droplets;
    (c) removing the solvent from the frozen droplets to produce friable microstructures;
    (d) forming a dispersion of the friable microstructures with at least one non-solvent for the biologically active agent; and
    (e) fragmenting the dispersed friable microstructures into submicron particles of biologically active agent.

2. The method of claim 1 wherein freezing is achieved by contacting the droplets with a cryogenic liquid.

3. The method of claim 2 wherein the cryogenic liquid is liquid nitrogen.

4. The method of claim 1 wherein the solvent is removed by lyophilization.

5. The method of claim 4 wherein lyophilization is conducted at a temperature below the lowest Tg of the frozen droplets.

6. The method of claim 1 wherein fragmentation is accomplished by homogenization, milling, sonication or a combination thereof.

7. The method of claim 6 wherein fragmentation is accomplished by sonication.

8. The method of claim 1 wherein the dispersion of friable microstructures further comprises at least one biocompatible polymer dissolved therein.

9. The method of claim 1 wherein the submicron particles have a volume median particle size of less than 1 micron, measured by laser diffraction.

10. The method of claim 1 wherein the biologically active agent is a protein or peptide.

11. The method of claim 10 wherein the protein is complexed to a stabilizing metal cation.

12. The method of claim 11 wherein said stabilizing metal cation is selected from the group consisting of $Zn^{+2}$, $Ca^{+2}$, $Cu^{+2}$, $Mg^{+2}$, $K^+$ and any combination thereof.

13. The method of claim 12 wherein the stabilizing metal cation is $Zn^{+2}$.

14. The method of claim 13 wherein the protein is recombinant human growth hormone.

15. The method of claim 1 wherein the dispersed system further comprises a metal cation component.

16. The method of claim 15 wherein the metal cation component is selected from the group consisting of $Mg(OH)_2$, $MgCO_3$, $CaCO_3$, $ZnCO_3$, $Mg(OAc)_2$, $Zn(OAc)_2$, $ZnSO_4$, $MgCl_2$, $ZnCl_2$, $MgSO_4$, zinc citrate and magnesium citrate.

17. A method for preparing a composition for the sustained release of biologically active agent comprising the steps of:

a) atomizing using multifluid atomization a dispersed system comprising at least one biologically active agent and at least one solvent at a mass flow ratio of about 0.30 or greater to produce droplets;

b) freezing the droplets to produce frozen droplets;

c) removing the solvent from the frozen droplets to produce friable microstructures;

d) dispersing the friable microstructures in at least one non-solvent for the biologically active agent;

e) fragmenting the dispersed friable microstructures to produce submicron particles of the biologically active agent;

f) providing a suspension comprising the submicron particles of the biologically active agent, at least one biocompatible polymer and at least one polymer solvent; and g) removing the polymer solvent to form a solid polymer/active agent matrix.

18. The method of claim 17 further comprising the steps of:

a) forming droplets of the polymer/active agent suspension;

b) freezing the droplets of the polymer/active agent suspension wherein steps a) and b) are performed prior to removing the polymer solvent; and c) removing the polymer solvent by extraction with an extraction solvent.

19. The method of claim 17 wherein the submicron particles have a volume median particle size of less than 1 micron, measured by laser diffraction.

20. The method of claim 17 wherein the biologically active agent is present in the suspension at a concentration of from about 0.01 to about 50% w/w of the combined weight of polymer and biologically active agent.

21. The method of claim 20 wherein the biologically active agent is present at a concentration of about 0.01 to 30% w/w of the combined weight of the polymer and biologically active agent.

22. The method of claim 17 wherein the biologically active agent is a protein or peptide.

23. The method of claim 22 wherein the biologically active agent is complexed to a stabilizing metal cation.

24. The method of claim 23 wherein said stabilizing metal cation is selected from the group consisting of $Zn^{+2}$, $Ca^{+2}$, $Cu^{+2}$, $Mg^{+2}$, $K^{+}$ and any combination thereof.

25. The method of claim 24 wherein said stabilizing metal cation is $Zn^{+}$.

26. The method of claim 22 wherein the protein is human growth hormone.

27. The method of claim 26 wherein the human growth hormone is complexed to $Zn^{+2}$.

28. The method of claim 17 wherein the biocompatible polymer is biodegradable.

29. The method of claim 28 wherein the biodegradable polymer is selected from the group consisting of poly(lactide)s, poly(glycolide)s, poly(lactide-coglycolide)s, poly(lactic acid)s, poly(glycolic acid)s, poly(lactic acid-co-glycolic acid)s, poly(caprolactone), polycarbonates, polyesteraniides, polyanhydrides, poly(amino acid)s, poly(ortho ester)s, polycyanoacrylates, polyamides, polyacetals, poly(ether ester)s, copolymers of poly(ethylene glycol) and poly(ortho ester)s, poly(dioxanone)s, poly(alkylene alkylate)s, biodegradable polyurethanes, blends and copolymers thereof.

30. The method of claim 29 wherein said polymer is poly(lactide-co-glycolide).

31. The method of claim 17 wherein the biocompalible polymer is non-biodegradable.

32. The method of claim 17 wherein the polymer solvent is methylene chloride, chloroform, acetone, ethyl acetate, methyl acetate, dimethylsulfoxide, hexafluoroisopropanol or any combinations thereof.

33. The method of claim 17 wherein the dispersed system further comprises a metal cation component which modulates the release of the biologically active agent from the composition for sustained release.

34. The method of claim 33 wherein the metal cation component is selected from the group consisting of $Mg(OH)_2$, $MgCO_3$, $CaCO_3$, $ZnCO_3$, $Mg(OAc)_2$, $Zn(OAc)_2$, $ZnSO_4$, $MgCl_2$, $ZnCl_2$, $MgSO_4$, zinc citrate and magnesium citrate.

35. The method of claim 17 wherein the suspension further comprises a metal cation component which modulates the release of the biologically active agent from the composition for sustained release.

36. A method for providing a therapeutically, prophylactically or diagnostically effective amount of a biologically active agent to a subject in need thereof for a sustained period comprising administering to the subject a dose of the sustained release composition prepared according to claim 17.

* * * * *